United States Patent [19]

Blanchard

[11] 3,964,317

[45] June 22, 1976

[54] DENSIMETER

[75] Inventor: Robert L. Blanchard, Lexington, Mass.

[73] Assignee: Foxboro/Trans-Sonics, Inc., Burlington, Mass.

[22] Filed: Nov. 18, 1974

[21] Appl. No.: 524,913

Related U.S. Application Data

[63] Continuation of Ser. No. 353,573, April 23, 1973, abandoned.

[52] U.S. Cl. .................................................. 73/453
[51] Int. Cl.$^2$ ......................................... G01N 9/18
[58] Field of Search ............. 73/453, 448, 451, 452; 235/151.3

[56] References Cited
UNITED STATES PATENTS

| | | |
|---|---|---|
| 3,054,296 | 9/1962 | Hargens et al. ........................ 73/453 |
| 3,126,745 | 3/1964 | Lütke ..................................... 73/453 |
| 3,184,975 | 5/1965 | Lindemann et al. ................... 73/453 |
| 3,407,666 | 10/1968 | Glassey ................................. 73/452 |
| 3,726,128 | 4/1973 | Fiet ..................................... 73/453 X |

*Primary Examiner*—Richard C. Queisser
*Assistant Examiner*—Stephen A. Kreitman
*Attorney, Agent, or Firm*—Cesari and McKenna

[57] ABSTRACT

A densimeter utilizes a low mass, neutral buoyancy float in association with a precision transducer which senses the deviation of the float position from a fixed neutral point corresponding to a predetermined fluid density within a range of fluid densities to be measured. The sensor output is accumulated and digitally added to a number corresponding to the predetermined density to thereby form an accurate representation of the fluid density.

4 Claims, 5 Drawing Figures

DENSIMETER

This is a continuation, of application Ser. No. 353,573 filed Apr. 23, 1973 now abandoned.

BACKGROUND OF THE INVENTION

A. Field of the Invention

The invention relates to a densimeter and, more particularly to a densimeter which utilizes a float to sense the density of a fluid.

B. Prior Art

Float type densimeters generally incorporate a float having a net positive buoyancy with respect to any fluid in which it might be immersed. The float is maintained at a selected reference position by means of forces applied to it. The force required to so maintain it is a measure of the density difference between the fluid in which the float is immersed and the overall density of the float; as the fluid density changes, the force is changed correspondingly.

Commonly, the force is applied to the float magnetically by means of a permanent magnet or a soft iron core attached to the float and magnetically coupled to a current carrying coil adjacent the float. The coil generates a field which interacts with the magnet or iron core and exerts a force on it. As the fluid density changes, the driving current in the coil is varied to maintain the float in its reference position. The current in the coil is a measure of the force applied and thus of the density of the fluid. This current is sensed to provide the density-indicating output of the instrument.

Densimeters of this type have several diadvantages. To begin with, since the float always has a net positive buoyancy with respect to the fluid in which it is immersed, the minimum value of its buoyancy is determined by the minimum density of the fluids in which it is intended to be immersed. Since the densimeter is to be operable over a wide range of densities, restoring forces of substantial magnitude are often required to return the float to its reference position. This in turn can require large driving currents in the force coil. We have found that the need to measure the current over a wide range is a cause of substantial error in density determination. Moreover, a large current generates significant heat which causes a temperature rise in the fluid surrounding the coil and this can materially affect the measured density of the fluid.

In addition to the foregoing sources of error, the greater the float buoyancy which must be offset by the restoring force, the greater will be the error due to variations in gravity. These variations change the required restoring force by an amount proportional to the magnitude of the buoyancy and thereby cause an error in the same proportion. Thus, when sensors of this type are installed on a vessel which moves about from place to place, an undesirably large error is introduced simply from variations in the gravitational constant from place to place.

A small float buoyancy, and thus small float volume is also desirable for minimizing the force required to restore the float to its neutral buoyancy position. However, present densimeters, by requiring the float to carry the weight of the magnet or iron used in the force rebalancing system, limit the extent to which the volume of the float can be reduced and thus require larger restoring forces with the consequent disadvantages noted above.

BRIEF DESCRIPTION OF THE INVENTION

A. Objects of the Invention

Accordingly, it is an object of the invention to provide an improved densimeter.

It is a further object of the invention to provide a densimeter capable of accurate density measurements over a broad range of fluid densities.

Another object of the invention is to provide an efficient force rebalancing system for a float-type densimeter.

Still another object of the invention is to provide a densimeter having a low error in response to changes in the gravitational constant.

BRIEF SUMMARY OF THE INVENTION

In accordance with the invention, the float of the present densimeter has a neutral buoyancy nominally at the center of the range of densities of a particular fluid in which the densimeter is to operate. A "loudspeaker type" force rebalancing motor is formed from inner and outer pole pieces defining an annular gap between them. A cylindrical coil connected to the end of a shaft connected to the float is positioned in this gap. A position sensor senses the displacement of the float from a reference position in response to departures in fluid density from the reference value thereof. The sensor output is used to control current through the coil. This current interacts with the magnetic field in the annular gap and thereby applies a rebalancing force to the float.

Because the float has a neutral buoyancy at the center of the density range to be measured, the rebalancing system need respond only to density changes whose magnitude is no more than half the range of the fluid densities to be monitored by the densimeter. This provides much greater absolute accuracy in the measurement of the current that rebalances the float. Further, the reduction in driving current minimizes errors from the heating effect of the current. Also, because of the reduced range of operation, the rebalancing system has greater linearity.

The rebalancing force structure also contributes to the improved accuracy and linearity. The balancing force generated by the preferred configuration is a highly linear function of the current applied to the coil. Also, the force system is highly efficient and the required driving current is thus less; this minimizes the heating effects as noted previously. Further, since the permanent magnet is stationary and only the driving coil is connected to the float, the magnet can be of substantial size and thus substantial field strength without requiring a corresponding increase in the float volume.

Because the density of the monitored fluid may be greater or less than the density of the float, the float in the present densimeter may have either a positive or negative buoyancy with respect to a particular fluid in which it is immersed. Consequently, unlike systems always having a net positive buoyancy, the restoring force may be upward or downward. Thus, the force rebalancing mechanism may either pull or push on the float. To avoid instability when the buoyant and restoring forces are directed toward each other, lateral restraints are provided for the float. Care should be taken to minimize the imposition of vertical restraining forces through such restraints, since this can seriously affect the system accuracy and linearity. In the present invention, the necessary lateral restraint is provided by two or more elongated, thin reeds cantilevered from the inner wall of the diameter of the densimeter casing and connected to the float at their innermost ends. These reeds are characterized by a high axial compliance and a high lateral stiffness, and thus provide lateral restraint without any significant vertical restraint.

The position sensor used to sense the displacements of the float from its neutral buoyancy position should also be quite sensitive. In the present invention this sensor is formed from a bobbin mounted on the float shaft and having an enlarged conductive core intermediate the float and the driving coil and a coil structure circumferentialy surrounding the core. The coil structure has a driving coil and a pair of sensing coils inside of which the core is free to move. The sensing coils are connected in electrical series with each other, and are symmetrically located with respect to the driving coil and the conductive core.

The driving coil generates a field which passes through the bobbin into the adjacent sensng coils. As long as the bobbin core is symmetrically located with respect to these coils, the voltages induced in the sensor coils are equal and opposite and therefore cancel. However, when the float and bobbin core are displaced from their reference position, the magnetic fluxes induced in the respective sensing coils are unequal and thus these coils provide a net output voltage across their terminals. This voltage is amplified and a driving current proportional to it is applied to the balancing system to return the float to its neutral position.

Unlike prior sensors of this type, the bobbin of the present invention is formed from a non-magnetic material, preferably aluminum. Thus, it is unaffected by the magnetic field of the force rebalancing system. The driver coil in the sensor establishes a position-dependent voltage in the sensing coils by setting up eddy current in the bobbin. These in turn create magnetic fields which counteract the field generated by the driver coil. The spatial location of these fields is determined by the bobbin position and thus the voltage induced in the sensing coils is correspondingly varied in accordance with bobbin position.

To establish the requisite eddy currents in the bobbin core, the sensor driver coil is driven from an alternating source in the kiloherz frequency range, e.g., 20 KHZ.

The float of the present densimeter is encased within a cylindrical tube whose diameter is slightly larger than the diameter of the float. The bottom of the shell is open so that fluid enters it and acts freely on the float. The shell in turn is centered within a baffle structure comprising three vertical wall segments extending around the arc of a circle and shielding the shell from sloshing of the liquid in which the densimeter is immersed. All these components are in turn encased with an outer shell having screened ports which admit liquid but screen out gross particulate material.

In calibrating the densimter, the float restoring current is preferably measured at two different fluid densities. One of these measurements may be made in air, while the other will generally be made in a fluid having a density within the range of densities to be measured.

DETAILED DESCRIPTION OF THE INVENTION

The foregoing and other and further objects and features of the invention will be more readily understood from the following detailed description of the invention when taken in conjunction with the accompanying drawings in which.

Figure 1:
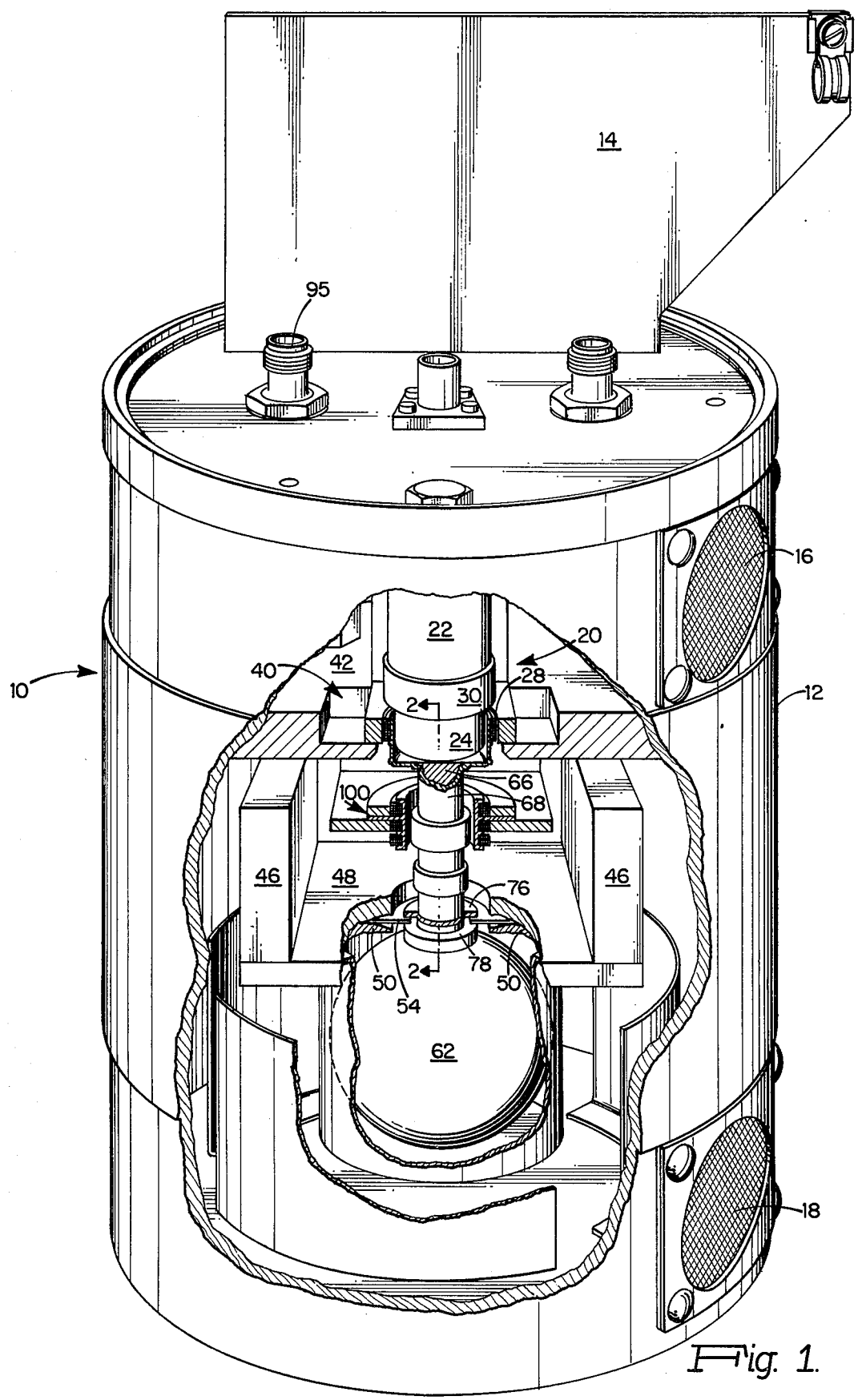
FIG. 1 is a view in perspective of a preferred embodiment of densimeter in accordance with the present invention, with portions broken away to show the construction and operation of the various components thereof.

In FIG. 1 a densimeter 10 has an outer casing 12 which is attached via a mounting plate 14 to a structure which supports it immersed in a fluid. Screened ports 16, 18 admit fluid to the interior of the casing 12, while screening out gross particulate material.

Figure 2:
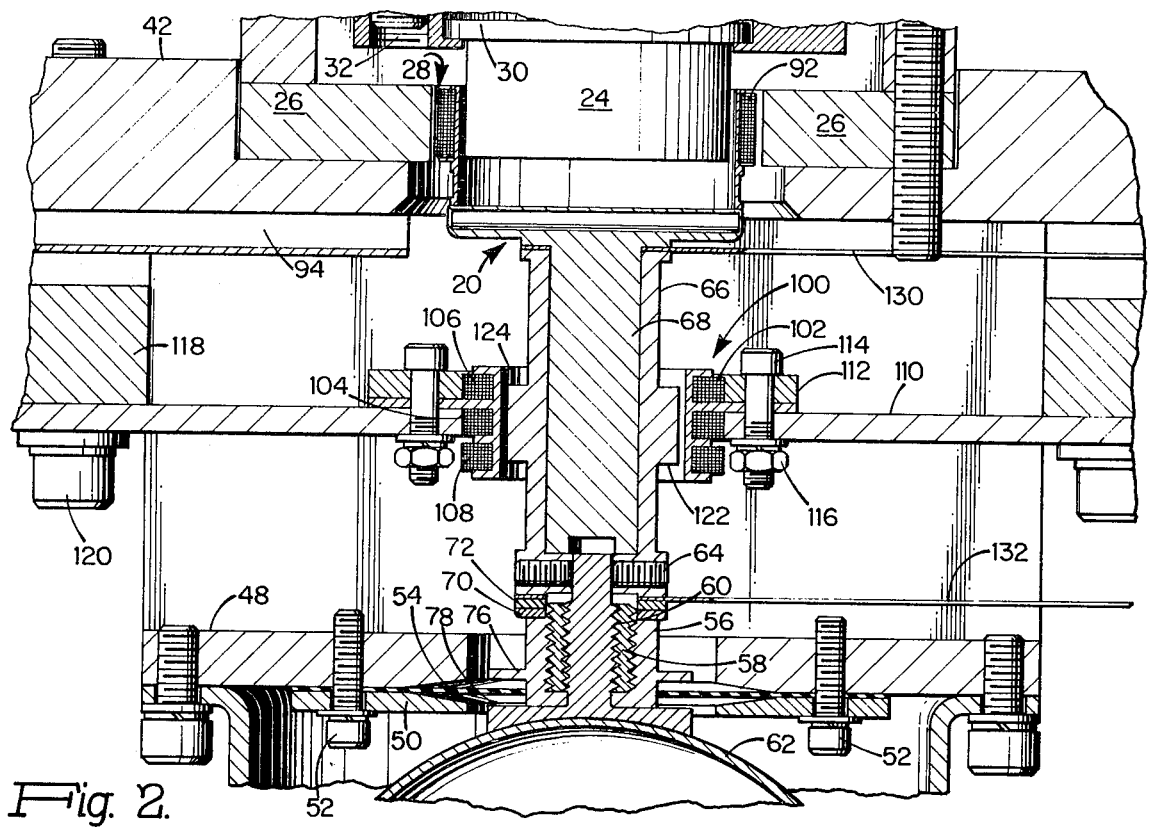
FIG. 2 is a partial vertical cross sectional view taken along the lines 2—2 of FIG. 1.

Referring now to FIG. 2, in connection with FIG. 1, a magnet structure 20 consisting of a cylindrical magnet 22, an iron pole piece 24 and a U-shaped flux guide 26 generates a radial magnetic field in a cylindrical air gap 28 formed between the pole piece 24 and the flux guide 26. The magnet 22 is supported from the flux guide 26 by means of a collar 30 and a number of retaining bolts 32 which extend between the upper portion of the guide 26 and collar 30.

Flux guide 26 rests on a recess 40 of a mounting plate 42. The plate 42 is mounted from the upper wall of housing 12 by conventional mounting means such as screws, bolts or the like. A further pair of mounting blocks 46 are attached to the lower face of mounting plate 42 and support, at the bottom thereof, a plate 48 having a collar 50 connected to the underside thereof by means of bolts 52. A thin, flexible, circular diaphragm 54 is clamped between the plate 48 and collar 50. The diaphragm 54 has a central aperture through which extends a cylindrical bushing 56 having a doubly threaded ring 58 on the interior thereof. Ring 58 retains the threaded stem 60 of a spherical hollow float 62. Lock screws 64 lock the stem 60 to a bobbin 66 carried on a core 68. Intermediate the bushing 56 and the bobbin 66 are a pair of spacer washers 70 and 72, and clamped between the washer 72 and the lower end of bobbin 66 is a reed 132 described in more detail hereinafter. Diaphragm 54 restrains the motion of float 54 to the range between an upper stop 76 on bushing 56 and lower stop 78 comprising the upper surface of stem 60. When the densimeter is free of fluid, stop 76 rests on diaphragm 54. When the float is immersed in a fluid whose density corresponds to the neutral buoyancy position, the diaphragm 54 is approximately midway between the stops 77 and 78.

The core 68 on which bobbin 66 is positioned carries at its upper end a cylindrical cup 90 onto which is wound a driving coil 92; this coil extends into the gap 28 between pole piece 24 and flux guide 26. Leads 94 extend from the float driving coil 92 to a connector 95 leading to the outside of the casing 12. When the coil 92 is energized, it creates a magnetic flux which reacts with the flux established in the gap 28 to create a force on the cup 90 and therefore on the core 68 and float 62. Because of the radial symmetry of the gap 28 and coil 92, this force is applied in a vertical direction, and is thus coincident with the longitudinal axis of the core 68 and the center of the spherical float 62 as long as the core is maintained in a vertical position; there is thus little, if any, side thrust applied to the core and float.

Figure 4B:
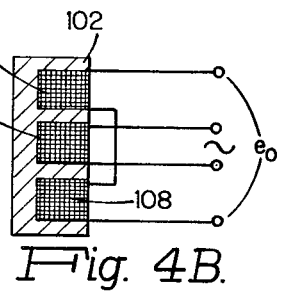
FIGS. 4A and 4B are sketches of the sensor coils.
Figure 4A:
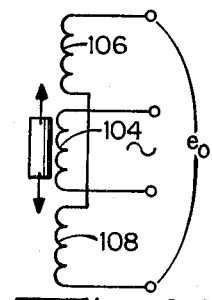

A position sensor 100 is located near the center of the core 68. The sensor comprises an enlarged cylindrical slug 122 on bobbin 66 spaced by an air gap 124 from a cylindrical coil form 102 surrounding the slug. A primary or driving winding 104 and a pair of secondary or sensor windings 106 and 108, respectively, are wound on coil form 102. The secondary windings are wound in the same direction on the coil form; as shown in FIG. 4A, they are electrically connected in series with each other and are coupled to the primary winding 104 only through magnetic coupling. Coil form 102 is mounted on a plate 110 by means of a cylindrical ring 112 and bolts 114 and nuts 116. Plate 110 in turn is connected to plate 42 by means of stand-offs 118 and bolts 120.

When the float 62 is positioned in a liquid whose density is greater than the density corresponding to the neutral buoyancy of the float, the dense liquid applies an upward thrust to the float which is counterbalanced by the downward thrust applied by the magnet 22 and the coil 92 as will shortly be described. If these two forces are not exactly coaxial, they will create an unbalanced couple which will tend to rotate the float and bobbin about the horizontal axis, thereby introducing error into any measurements made during this condition. To prevent this, the core 68 and thus the float 62 are restrained in lateral movement by means of a pair of long, flat, thin, narrow reeds 130, 132 connected in cantilever fashion between the upper and lower segments of the core 68 and a post 134 (FIG. 1) adjacent the inner wall of casing 12. They have a circular aperture slightly larger in diameter than the core 68 at their innermost end so as to snugly engage this core. These reeds, which are preferably made of a material such as stainless steel, have a high compliance in their thin direction (the vertical direction) but have great resistance to bending in the direction of their width. (the horizontal direction). Thus, they provide very little resistance to the motion of the core 68 in the vertical direction, but provide strong lateral restraint.

Figure 3:
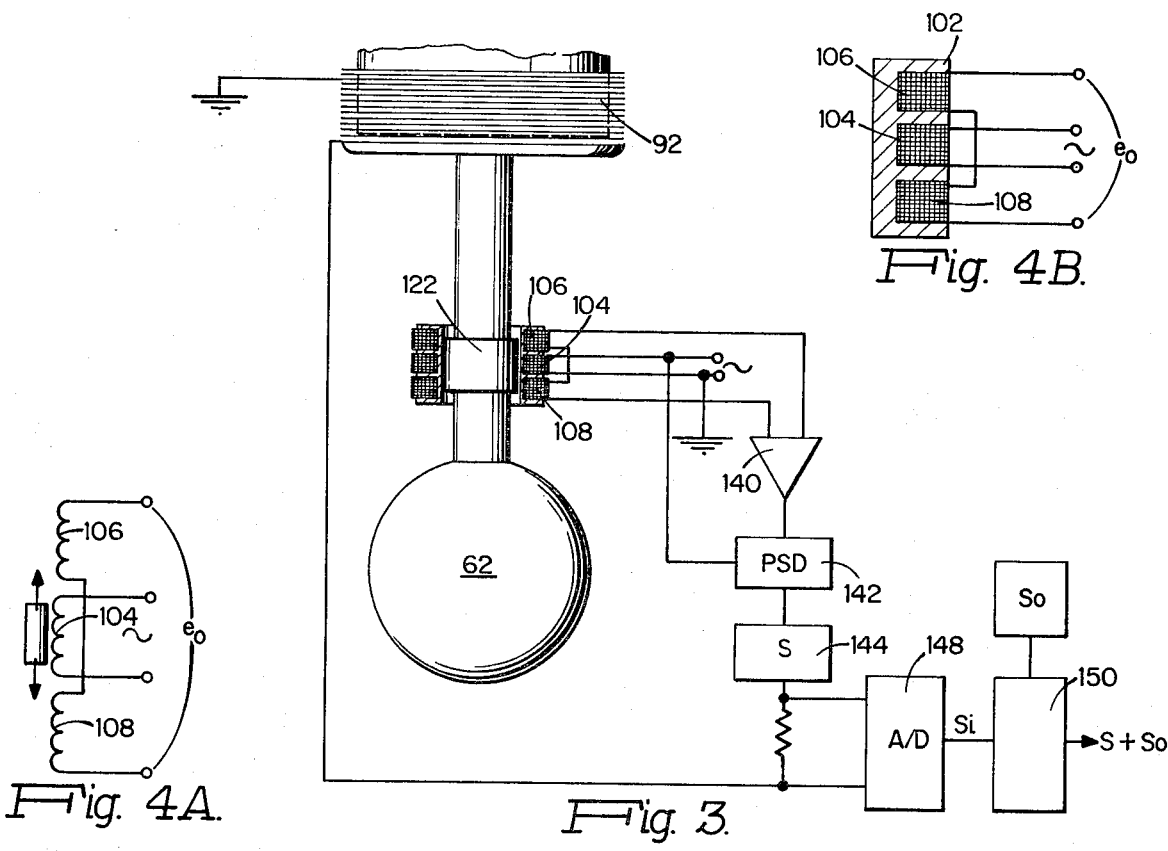
FIG. 3 is a diagrammatic sketch of the sensing and float rebalancing portions of the densimeter.

Turning now to FIG. 3, the electrical circuitry of the float rebalancing system is shown in detail. The coil 104 is energized from a source of alternating voltage (not shown). This creates eddy currents in the bobbin 66 and slug 122 and these establish magnetic fields which partially oppose the field established by coil 104 and thus modify the flux coupled to coils 106 and 108. When the cylindrical cross section 122 of the bobbin 66 is symmetrically positioned with respect to the coils 106 and 108 as shown in FIGS. 2 and 3, equal and opposite flux are induced in these coils and thus the net flux across the series-connected coils is zero. When, however, the cylindrical cross section 122 is vertically displaced from the position shown, it covers more of one of the coils 106, 108 and less of the other, and thus unequal fluxes are induced in these coils in response to the driving voltage applied to the coil 104.

The net voltage applied across the coils 106 and 108 in series is applied to a difference amplifier 140 and thence to a phase sensitive detector 142 which also is connected to receive the same driving voltage applied to the coil 104. The detector 142 essentially "rectifies" the alternating voltage applied to it by the amplifier 140. An integrator 144 integrates the output of the detector 142 and applies a steady driving current to the coil 92 through a resistor 146 to restore the float to its zero or "neutral buoyancy" position. The magnitude and direction of this current is a direct measure of the force required to restore the float to its neutral buoyancy position and thus is a measure of the density increment of the fluid in which the float is immersed relative to the neutral buoyancy density. The current is sensed by an analog to digital converter 148 (serving as a digital volt meter) and the output of converter 148 is applied to a calculator 150. A digital number representing the "neutral buoyancy" density $\rho_o$ of the densimeter is digitally added to the incremental density $\rho_i$. The resultant sum is the desired fluid density.

Converting the current corresponding to the incremental density from analog to digital form prior to addition to the neutral buoyancy density further minimizes errors in the system. In prior densimeters, the output of the densimeter was an analog voltage corresponding to the total density of the fluid in which the densimeter was immersed. Slight changes in density from one liquid to another produced only small changes in the analog output signal and these small changes were more readily obscured by noise or even small imperfections in the measuring instrument. In the present system, however, only the incremental density $\rho_i$ is sensed and this therefore can be measured with much greater accuracy. Further, by converting it to digital form prior to its addition to the neutral buoyancy density $\rho_o$, one can effectively reduce to zero the uncertainty introduced by the addition process. Thus, the density of the fluid can be determined very accurately, and even small changes in density from one fluid to the next can readily be detected.

The present invention is especially suited to measuring fluid densities in commercial tankers or the like which carry fluids such as liquid natural gas (LNG) whose density must be measured with an accuracy of 0.1% over a density of from 0.44 to 0.52 grams per milliliter (gm./ml.) or of a class of fluids such as LNG-LPG, ethylene and butadiene whose density must be accurately measured (e.g., within 0.5%) over a density range of from 0.42 to 0.67 gm./ml.

From the foregoing it will be seen that I have provided an improved densimeter. The densimeter described herein measures a range of densities with great accuracy and sensitivity. It has an improved force system minimizng the weight to be carried by the spherical float, and thus allows greater freedom of design in connection with this float, as well as in the selection of the magnet structure and its desired strength. A simple sensor unaffected by the magnetic force rebalancing system provides an accurate indication of displacement of the densimeter float from its zero buoyancy position. System accuracy is maintained through use of digital summation of the neutral buoyancy density and the density increment from a particular liquid.

It will be perceived from the foregoing that various changes may be made in the illustrative embodiments illustrated and described herein without departing from the spirit and scope of the invention. For example, instead of applying the driving voltage to the coil 104 and measuring the voltage induced across the coils 106 and 108, the driving voltage may be applied to the coils 106 and 108 and the voltage across coil 104 used to rebalance the system. Other changes will suggest themselves to those skilled in the art.

I claim:
1. A densimeter, comprising:
   A. a housing for complete immersion in a cryogenic liquid whose density is to be measured and ported to admit to the interior thereof said liquid;

B. a float in said housing, said float having a neutral buoyancy position in said housing at the center of a range of densities of the liquid to be measured and mounted for vertical movement in response to changes in the density of said liquid;

C. a permanent magnet in said housing;

D. a force coil in said housing carrying a restoring current mounted for movement with said float and positioned to cooperate with said magnet to apply both upward and downward forces to said float to restore it to its neutral buoyancy position in response to departures therefrom caused by its immersion in liquids of lesser and greater density respectively, said coil carrying a current proportional to the difference between the density of said liquid and the density corresponding to the neutral buoyancy position of said float and generating heating losses corresponding to such difference only.

2. A densimeter according to claim 1 which includes:

A. a digital storage register for storing a first digital signal corresponding to said neutral buoyancy density;

B. means for generating a second digital signal indicative of the magnitude of said restoring current in said coil, and C. means for adding said signals to thereby provide an accurate digital indication of the density of said liquid.

3. A densimeter according to claim 1 which includes a position sensor comprising:

A. an electrically conductive, non-magnetic core mounted for movement with said float;

B. a driving coil positioned to induce eddy currents in said core when energized with an alternating voltage;

C. a pair of sensing coils, symmetrically mounted with respect to said core when said float is at its neutral buoyancy position and connected in series-opposition, said sensing coils being positioned to intercept magnetic fields generated by said driving coil and by the eddy currents in said core, and providing an output indicative of the displacement of said core from the neutral buoyancy position.

4. A densimeter according to claim 3 including means responsive to the output of said sensing coils to simultaneously apply said restoring current to said force coil and apply a signal indicative of said current to an indicator circuit to thereby provide an indication of the extent of the departure of said density from the density corresponding to the neutral buoyancy position of said float.

* * * * *